US006544212B2

(12) United States Patent
Galley et al.

(10) Patent No.: US 6,544,212 B2
(45) Date of Patent: Apr. 8, 2003

(54) DIABETES MANAGEMENT SYSTEM

(75) Inventors: Paul J. Galley, Indianapolis, IN (US); Ajay Thukral, Indianapolis, IN (US); Siva K. Chittajallu, Indianapolis, IN (US); Stefan Weinert, Pendleton, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/918,623

(22) Filed: Jul. 31, 2001

(65) Prior Publication Data

US 2003/0028089 A1 Feb. 6, 2003

(51) Int. Cl.[7] .......................... A61M 1/00; A61M 31/00
(52) U.S. Cl. ......................................... 604/31; 604/504
(58) Field of Search ................... 604/31, 48, 500–504, 604/131

(56) References Cited

U.S. PATENT DOCUMENTS

| | | | | |
|---|---|---|---|---|
| 4,282,872 A | | 8/1981 | Franetzki et al. ............ 128/213 |
| 4,731,726 A | | 3/1988 | Allen, III .................... 364/416 |
| 4,777,953 A | | 10/1988 | Ash et al. .................... 128/635 |
| 5,019,974 A | | 5/1991 | Beckers ................. 364/413.02 |
| 5,174,291 A | | 12/1992 | Schoonen .................... 128/632 |
| 5,216,597 A | | 6/1993 | Beckers ................. 364/413.02 |
| 5,222,496 A | | 6/1993 | Clarke et al. ................ 128/633 |
| 5,251,126 A | | 10/1993 | Kahn et al. ............. 364/413.11 |
| 5,364,346 A | * | 11/1994 | Schrezenmeir .............. 604/504 |
| 5,507,288 A | | 4/1996 | Bocker et al. ............... 128/633 |
| 5,665,065 A | * | 9/1997 | Colman et al. ............... 604/66 |
| 5,730,714 A | | 3/1998 | Guy et al. ..................... 604/20 |
| 5,822,715 A | | 10/1998 | Worthington et al. ......... 702/19 |
| 5,840,020 A | | 11/1998 | Heinonen et al. ........... 600/309 |
| 5,855,616 A | | 1/1999 | Fournier et al. ............... 623/11 |
| 5,989,917 A | | 11/1999 | McAleer et al. .............. 436/46 |
| 5,997,475 A | | 12/1999 | Bortz ........................... 600/300 |
| 6,023,009 A | | 2/2000 | Stegemann et al. ........... 623/11 |
| 6,024,699 A | | 2/2000 | Surwit et al. ................ 600/300 |
| 6,027,692 A | | 2/2000 | Galen et al. .............. 422/82.05 |
| 6,049,727 A | | 4/2000 | Crothall ....................... 600/310 |
| 6,061,582 A | | 5/2000 | Small et al. ................. 600/316 |
| 6,269,314 B1 | | 7/2001 | Iitawaki et al. ............... 702/23 |

FOREIGN PATENT DOCUMENTS

| | | |
|---|---|---|
| DE | 27 58 467 | 8/1981 |
| DE | 42 21 848 A1 | 1/1994 |
| DE | 44 15 896 | 11/1995 |
| DE | 197 25 676 A1 | 12/1998 |
| EP | 0 290 683 A2 | 11/1988 |
| EP | 0 462 466 A2 | 12/1991 |
| EP | 0 483 595 | 5/1992 |
| EP | 0 824 240 | 2/1998 |

(List continued on next page.)

OTHER PUBLICATIONS

Parker et al. "A Model–Based Algorithm for Blood Glucose Control in Type I Diabetic Patients", IEEE Transactions on Biomedical Engineering, vol. 46, No. 2, Feb. 1999, pp. 148–157.

(List continued on next page.)

Primary Examiner—Sharon Kennedy
(74) Attorney, Agent, or Firm—Jill L. Woodburn

(57) ABSTRACT

A system is provided that enables glycemic control for a subject. The system includes an insulin delivery unit, a glucose sensor, and a control unit. The control unit includes a processor unit that receives glucose value readings from the glucose sensor, executes an algorithm that predicts a glucose value at a predetermined time in the future, compares that predicted glucose value to a pre-determined glucose value range, and determines a corrective amount of insulin to be administered when the predictive glucose value lies outside of the predetermined glucose value range. The control unit also includes a communication unit that transmits the corrective amount to the delivery unit.

25 Claims, 8 Drawing Sheets

FOREIGN PATENT DOCUMENTS

| | | |
|---|---|---|
| EP | 0 881 495 A1 | 12/1998 |
| EP | 1 102 194 A2 | 5/2001 |
| GB | 2 218 831 | 11/1989 |
| WO | WO 97/28737 | 8/1997 |
| WO | WO 00/53257 A1 | 3/2000 |
| WO | WO 00/18293 | 4/2000 |
| WO | WO 00/74753 | 12/2000 |
| WO | 01/58511 A1 | 8/2001 |

OTHER PUBLICATIONS

Rutscher et al., "KADIS: Model–Aided Education in Type I Diabetes", Computer methods and Programs in Biomedicine 41 (1994) 205–215.

Shimoda et al. "Closed–Loop Subcutaneous Insulin Infusion Algorithm with a Short Acting Insulin Analog for LongTerm Clinical Application of a Wearable Artificial Endocrine Pancreas", Frontiers Med. Biol. Engng, vol. 8 No. 3 pp. 197–211 (1997).

Shichiri et al. "Enhanced, Simplified Glucose Sensors: Long–Term Clinical Application of Wearable Artificial Endocrine Pancreas", Artificial Organs, 22(1): 32–42, Blackwell Science, Inc. (1998).

* cited by examiner

DIABETES MANAGEMENT SYSTEM

FIELD OF THE INVENTION

The present invention relates to a system for managing diabetes. More particularly, the present invention relates to an automated system for determining the timing and amount of insulin administration to a subject in the treatment of diabetes.

BACKGROUND AND SUMMARY OF THE INVENTION

Typically, insulin therapy is based upon a set of rules that employ periodic glucose measurements to make insulin recommendations to manage glucose levels. The rules are based on estimates of an individual subject's response to carbohydrates, insulin and exercise. In practice, these rules are used to present an initial therapy. The subject then individualizes this therapy with the help of a health-care provider by analyzing the glycemic results achieved to date. This data is in the form of a written or electronic logbook that the subject maintains regarding exercise, food consumption, insulin doses and glucose measurements. The rules are applied for administering insulin and/or carbohydrates based on experience and abnormal glucose values. Rules are generally updated when the therapy results in degraded blood glucose control.

Electronic diabetes management systems have been developed to assist subjects in the implementation of insulin administration regimens. See, for example U.S. Pat. Nos. 5,019,974; 4,731,726; 5,822,715; 5,840,020. See also, EP 1 102 194 A2, the disclosure of which is incorporated herein by reference.

According to the present invention, a system for providing glycemic control to a subject is provided. The system comprises an insulin delivery unit, a glucose sensor, and a control unit. The control unit includes a processor unit that receives glucose value readings from the glucose sensor, executes an algorithm that predicts a glucose value at a pre-determined time in the future, compares that predicted glucose value to a pre-determined glucose value range, and determines a corrective amount of insulin to be administered when the predictive glucose value lies outside of the pre-determined glucose value range. The control unit also includes a communication unit that transmits the corrective amount to the delivery unit. In at least one embodiment, a predictive model is provided that is based on the following equation: $\Delta G = -(TotalInsuRemain - BasalReq) * Sensitivity$, wherein $\Delta G$=future change in glucose level at a pre-determined time, TotalInsuRemain=amount of insulin remaining in the subject's system at the current time, BasalReq=how much insulin the subject is estimated to need at the pre-determined time, and Sensitivity=Insulin sensitivity.

In addition, a system for providing glycemic control to a subject is provided in accordance with the present invention. The system comprises a sensor formed to conduct a glucose measurement of a subject, a control unit that includes a processor unit that is formed to accept data from the subject on insulin sensitivity and basal rate, to execute an algorithm that generates a predictive value of the subject's glucose level at a predetermined time in the future based upon the glucose measurement from the sensor and the data, and to compute a corrective action when the predictive value lies outside of a predetermined target range. The system also includes an insulin delivery unit in communication with the control unit. The delivery unit is formed to administer automatically a dosage of insulin to the subject based upon the computed corrective action of the control unit.

Still further in accordance with the present invention a method for providing glycemic control to a subject is provided. The method comprises the steps of determining the glucose value of a subject and inputting the glucose value into at least one processor. The at least one processor is formed to execute at least one algorithm that anticipates the future effects of insulin that has been previously delivered to the subject, to incorporate constraints on insulin delivery and glucose deviations, and to determine a corrective amount of insulin to be administered when the predictive glucose value lies outside of the pre-determined glucose value range. Next, the desired insulin dosage is delivered automatically to the subject and both the determining and inputting steps are repeated.

In addition, a system for providing glycemic control to a subject is provided. The system comprises means for delivering insulin to a subject, means for determining a glucose value from the subject, and a control unit including a processor unit that is formed to compare the glucose value to a predetermined glucose value range. The processor unit is also formed to determine a corrective amount of insulin to be administered when the predictive glucose value lies outside of the pre- determined glucose value range and to transmit the corrective amount to the delivering means.

According to another embodiment of the present invention a system for predicting a future glucose value of a subject at a predetermined time is provided. The system comprises a control unit that includes a processor unit formed to predict the future glucose value with an algorithm $\Delta G = -(TotalInsuRemain - BasalReq) * Sensitivity$, wherein $\Delta G$=future change in glucose levels at a pre-determined time, TotalInsuRemain=amount of insulin remaining in the subject's system at a current time, and BasaiReq=how much insulin the subject is estimated to need to maintain the current glucose level, and Sensitivity=Insulin sensitivity.

According to still another embodiment of the present invention a system for recommending an insulin dose that compensates for meals for a subject is provided. The system comprises a control unit that includes a processor unit formed to compensate for meals with a feedforward algorithm Dose=carbohydrates * insulin-to-carb-ratio * $\alpha_{meal\ type}$—intercept, wherein Dose=Insulin dose, carbohydrates= grams of carbohydrates, insulin-to-carb-ratio=Insulin to Carbohydrate Ratio, $\alpha_{meal\ type}$=meal dependent scaling factor, and intercept=intercept to allow a linear fit for sizes of the meals.

Additional features of the invention will become apparent to those skilled in the art upon consideration of the following detailed description of the preferred embodiment exemplifying the best mode of carrying out the invention

BRIEF DESCRIPTION OF THE DRAWINGS

The detailed description particularly refers to the accompanying figures in which.

DETAILED DESCRIPTION OF THE DRAWINGS

A subject with diabetes is confronted with ongoing therapeutic decisions to manage their disease effectively. This management requires an understanding of the subject's response to meals, exercise, insulin, stress, alcohol, medication, hormones, illness, and a number of other factors that interact in complex ways. Management requires complex calculations, glucose measurements, and insulin injections.

In an effort to manage the disease, individuals may elect to make a transition from multiple daily spot glucose measurements to continuous glucose monitoring. The system of the present invention incorporates algorithms with continuous feedback for glycemic control that enables management with continuous monitoring. One embodiment of the present involves subcutaneous glucose monitoring and subcutaneous delivery of rapid-acting insulin (e.g. HUMALOG®, Eli Lilly and Company, Indianapolis, Ind. or NOVORAPID®, Novo Nordisk A/S, Bagsvaerd, Denmark). In addition to time-dependent variations of physiological conditions, the control algorithm compensates for delays on the measurement side (physical or technology-related lags and physiological lags between subcutaneous space and blood) as well as on the delivery side (delayed insulin action due to peripheral delivery). In order to achieve acceptable glycemic control, especially under disturbance challenges of meals and physical activity, feedback-based insulin dose adjustment is used in a feedback algorithm. Further, a feedforward algorithm is notified of pending meals in advance and this notification generally includes information about size (carbohydrate amount) and type of the meal (relative speed of the meal) to be ingested.

Thus, the system of the present invention permits the individual to manage their diabetes with minimal intervention with near normal glycemic control. This system uses qualitative and quantitative information regarding interstitial glucose values and administered insulin to determine the timing and amount of insulin administration, and preferably carbohydrate intake recommendations. Additional information, such as meals, exercise, stress, illness, and alcohol consumption may also be utilized by the system in accordance with this disclosure. In preferred embodiments, the system of the present invention analyzes past data to make modifications to the existing therapy.

Figure 1:
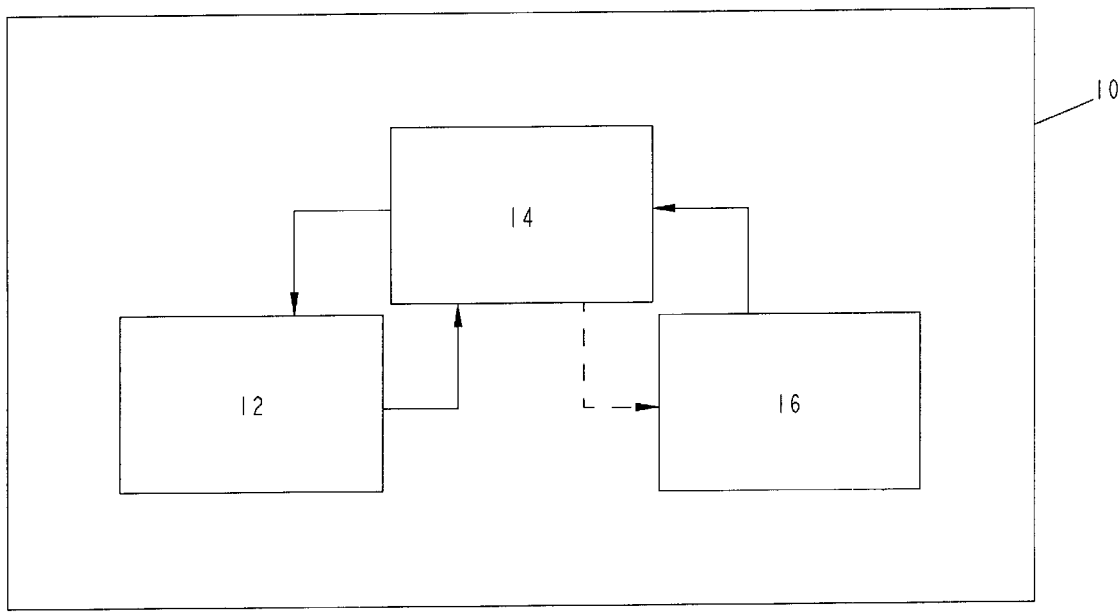
FIG. 1 is a schematic of the system of the present invention.

This system 10 in accordance with the present invention comprises an insulin delivery unit 12, a glucose sensor 16, and a control unit 14. See FIG. 1. The concentration of interstitial glucose in a diabetic changes due to external influences, non-limiting examples of which include insulin administration, meals and exercise. Sensor 16 measures the glucose and reports the value to control unit 14. Control unit 14 responds to the measured glucose levels by determining the appropriate amount of insulin to administer in order to normalize glucose levels within a pre-determined target range. This target range for glucose is from about 60 mg/dl to about 250 mg/dl, preferably about 80 mg/dl to about 210 mg/dl, and most preferably about 90 mg/dl to about 150 mg/dl. It is appreciated, however, that the target range may exceed the range of about 60 mg/dl to about 250 mg/dl in accordance with this disclosure based upon the individualized needs of the subject. Control unit 14 then directs delivery unit 12 to administer the appropriate amount of insulin to the subject.

In at least one embodiment, control unit 14 also stores feedback and feedforward algorithms, the glucose concentrations, and the amount of insulin administered as well as the times of administration in a memory unit. It is further appreciated that the memory unit may also store the carbohydrates consumed and the times they were consumed as well as the duration and intensity of any exercise performed by the subject. This memory is formed with memory components, a non-limiting example of which is known as RAM, which is well known in the prior art.

The system of the present invention operates upon an assumption that there exists an insulin basal rate for a subject that is required to maintain a steady-state glucose level (G) at a specified therapy level. It is understood that this basal rate can be either a fixed value or vary with time. Based upon this basal rate, it is possible to select an insulin infusion rate to meet the target range of the desirable glucose level. The system of the present invention utilizes this pre-determined basal rate in making its insulin dosage recommendations in order to hold the glucose level within the target range. It is appreciated that this basal rate is individualized and can be determined using a variety of well known methods.

Insulin delivery unit 12 is formed to administer automatically a dosage of insulin to the subject based upon the computed corrective action of the control unit 14. Operation of delivery unit 12 depends upon subject-specific recommendations from control unit 14 and occurs at a pre-determined time interval or cycle. It is appreciated that unit 12 can deliver a variety of insulin doses in accordance with this disclosure. Insulin dosages generally range from 0 U to about 15 U per cycle, which are based upon the projected insulin needs of the subject. It is appreciated that while these time intervals or cycles can vary, non-limiting examples of appropriate time intervals range from about 1 minute to about 1 hour, preferably 5 minutes to about 30 minutes, most preferably about 10 minutes. Delivery unit 12 can be a continuous type system(e.g. an "insulin pump) a semi continuous system, or a discrete delivery system. In addition, delivery unit 12 can be any one of a variety of commercially available delivery units in accordance with this disclosure. A non-limiting example of a suitable semi-continuous delivery unit is a H-Tron Insulin pump, commercially available from Disetronic Medical Systems, Inc., St. Paul, Minn. Non-limiting examples of suitable discrete delivery units include B-D® PEN Insulin Delivery Device, commercially available from BD, Franklin Lakes, N.J. and the Lilly Pen, commercially available from Eli Lilly and Company, Indianapolis, Ind.

Glucose sensor 16 draws a body fluid sample from a subject for testing. Operation of sensor 16 occurs at a pre-determined time interval or cycle. This time interval preferably corresponds with the time intervals of the operation of delivery unit 12. In use, sensor 16 draws samples from the subject about every 1 minute to about 1 hour, more preferably about every 5 minutes to about 20 minutes, most preferably about every 10 minutes. Sensor 16 can be a continuous glucose-sensing unit, a semi-continuous glucose-sensing unit, or a discrete glucose-sensing unit. Further, suitable glucose sensors may be electrochemical, microdialysis, transdermal, or noninvasive.

For example, electrochemical glucose sensors are known in which glucose concentration can be measured in a capillary blood sample collected by the subject from the fingertip and then applied to a test element, for instance. A device based on sampling blood is described in U.S. Pat. Nos. 5,288,636; 5,053,199; 5,366,609; and 4,891,319 the disclosures of each of which are hereby incorporated herein by reference. To determine glucose values, it is also possible to implant electrochemical measurement sensors in the body (e.g., intravasal, interstitial). See, for example the MiniMed Continuous Glucose Monitoring System —CGMS—, commercially available from MiniMed Inc. Northridge, Calif.

Another possibility for the determination of glucose values is based on measurements in interstitial fluid. Devices are known with which small quantities of interstitial fluid can be collected through thin cannula and then analyzed. To perform subcutaneous measurements it is also possible to implant miniaturized catheters with which microdialysis or ultrafiltration can be performed, so that measured results can be provided at close intervals. A device based on microdialysis is described in U.S. Pat. No. 5,174,291, the disclosure of which is incorporated herein by reference. A device based on ultrafiltration is described in U.S. Pat. No. 4,777,953, the disclosure of which is incorporated herein by reference. An example of an implantable sensor is disclosed in U.S. Pat. No. 6,049,727, the disclosure of which is incorporated herein by reference.

Further, non-invasive sensors are suitable in accordance with this disclosure. Non-limiting examples of such known sensors include GLUCOWATCH®Biographer, commercially available from Cygnus, Inc., Redwood City, Calif., as well as sensors disclosed in U.S. Pat. Nos. 5,730,714, 5,222,496, and 6,061,582, the disclosures of each of which are incorporated herein by reference. It is appreciated that sensor 16 can be any one of a variety of in vivo or in vitro sensors in accordance with this disclosure. Since samples are drawn from a subject frequently, it is preferred that sensor 16 be implanted in the subject, such as the CGMS as described above.

Sensor 16 does not generally produce a glucose reading instantaneously, but rather, a period of time elapses between the time that a sample is extracted from the subject and the time that the glucose measurement is available from use by unit 14. This time delay can range from about 1 minute to about 45 minutes, more typically from about 5 minutes to about 30 minutes, and most typically, the time delay for the glucose measurement is about 5 to about 15 minutes. System of the present invention recognizes that this time delay exists and control unit 14 is formed to compensate, or make corrections for the delay. It is also appreciated that a sensor may be used in the system of the present invention, which reduces or even eliminates this time delay.

Control unit 14, is formed to predict the current glucose value of the subject based upon the delayed glucose reading, the history of insulin infusions, the basal requirement, and the insulin sensitivity of the subject. Insulin sensitivity is defined herein as the expected drop of glucose concentration when 1 U of insulin is administered to the subject. It is understood that insulin sensitivity is individual to the subject and is determined over a period of time.

Unit 14 includes a processor unit that executes an algorithm to determine an insulin dosage recommendation and a communication unit that forwards that recommendation of the processor unit to the delivery unit 12. It is appreciated that non-limiting examples of suitable processor units include microprocessors, portable laptop computers, or mainframe computers. The communication unit or units can be of the type of a serial port, a RF port, an IR port, an ultrasound mode, or any number of commercially available communication units. Non-limiting examples of power sources suitable to power the processing and communication units can be solar power, battery power (throw away or rechargeable), conventional AC power, or mechanical power in accordance with this disclosure. It is appreciated that processor unit and communication unit can be assembled in one single device, or they can be discrete devices that communicate with each other through wired or wireless means (IR link or RF link).

The processor unit of control unit 14 is a microprocessor. It is appreciated that the microprocessor may be any number of commercially available microprocessors. A non-limiting example of a suitable microprocessor includes a personal digital assistant (PDA) that includes a display. The display enables the subject to input data and review data from unit 14. Non-limiting examples of data displayed by unit 14 includes the glucose values, insulin doses and their times of administration, the carbohydrates consumed or to be consumed and the times they are consumed, and exercise performed or to be performed, the duration of the exercise, and the intensity of the exercise. In addition, non-limiting examples of the display include a data input unit with a visual display unit and/or an auditory/vibratory feedback unit in accordance with this disclosure. It is appreciated that data can also be inputted via a keyboard.

In addition, to processor unit and communication unit, the control unit 14 of the present invention preferably includes a memory unit. The memory unit stores the algorithms, the glucose concentrations, the amount of insulin administered, the times of administration, the carbohydrates consumed, the times the carbohydrates were consumed, and the duration and intensity of any exercise performed by the subject. The memory unit is formed with memory components, non-limiting examples of which include a RAM unit, a disk drive unit, a hard disk drive unit, a tape drive unit, or other data storage means, which are well known in the art. It is appreciated that the memory unit may be a discrete component rather than integral with the processor and communication units.

Figure 5:
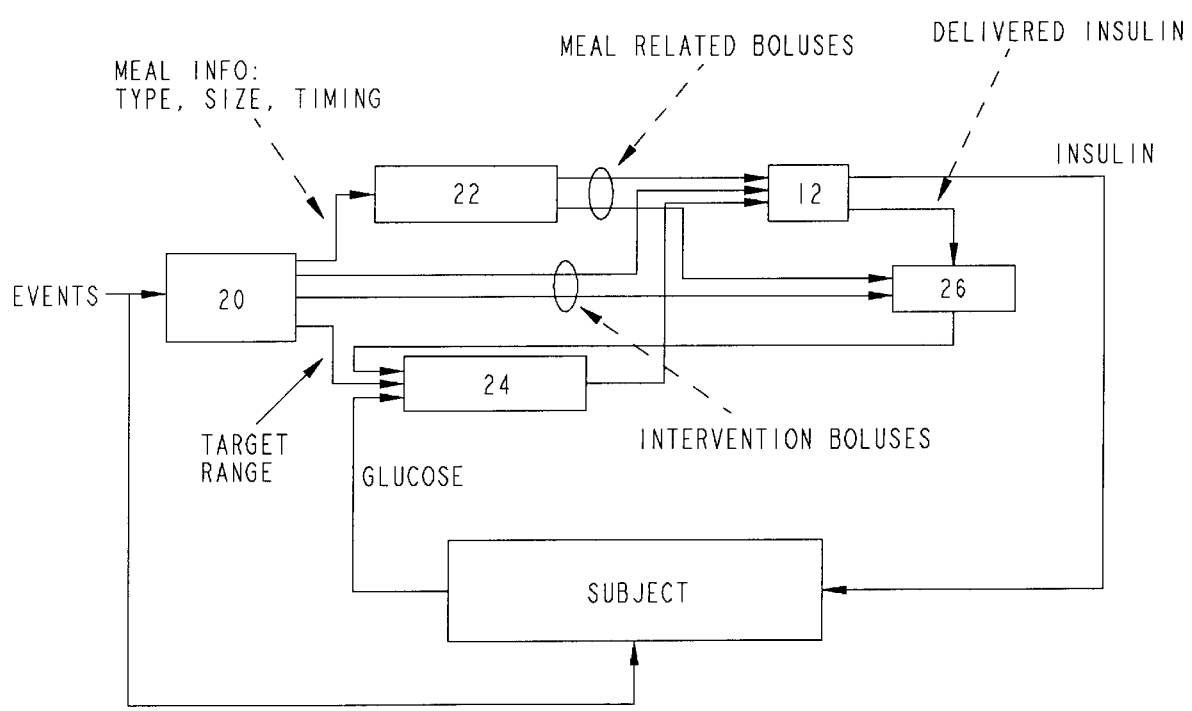
FIG. 5 is a graph showing an assumed shape of the insulin effect on a subject for purposes of an empirical algorithm.
Figure 7:
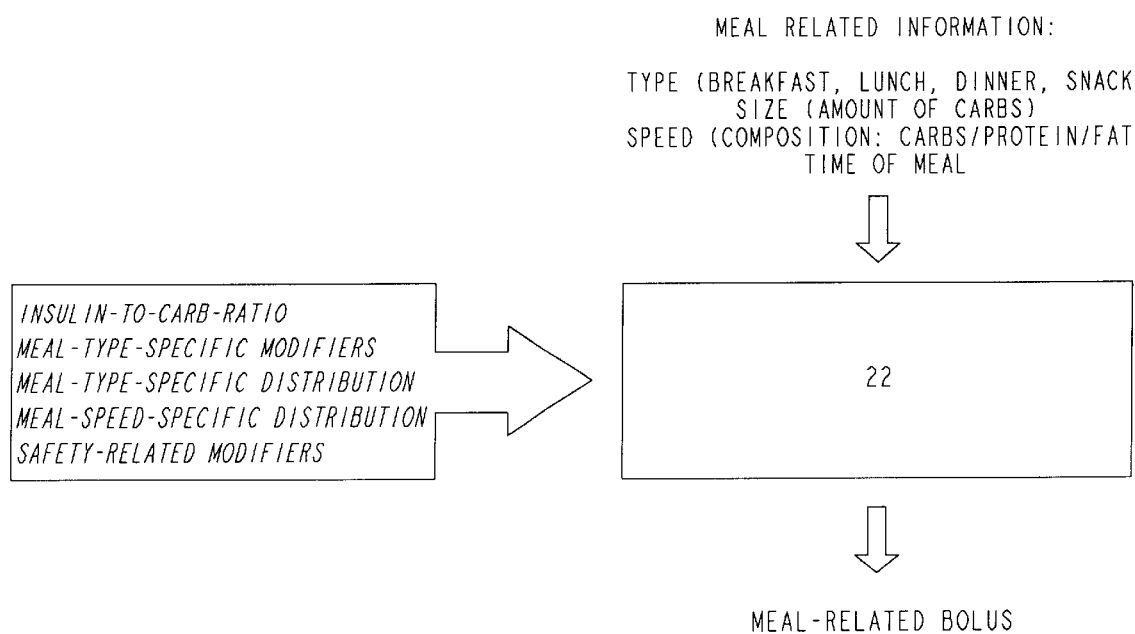
FIG. 7 is a schematic of a portion of the system of FIG. 4.
Figure 8:
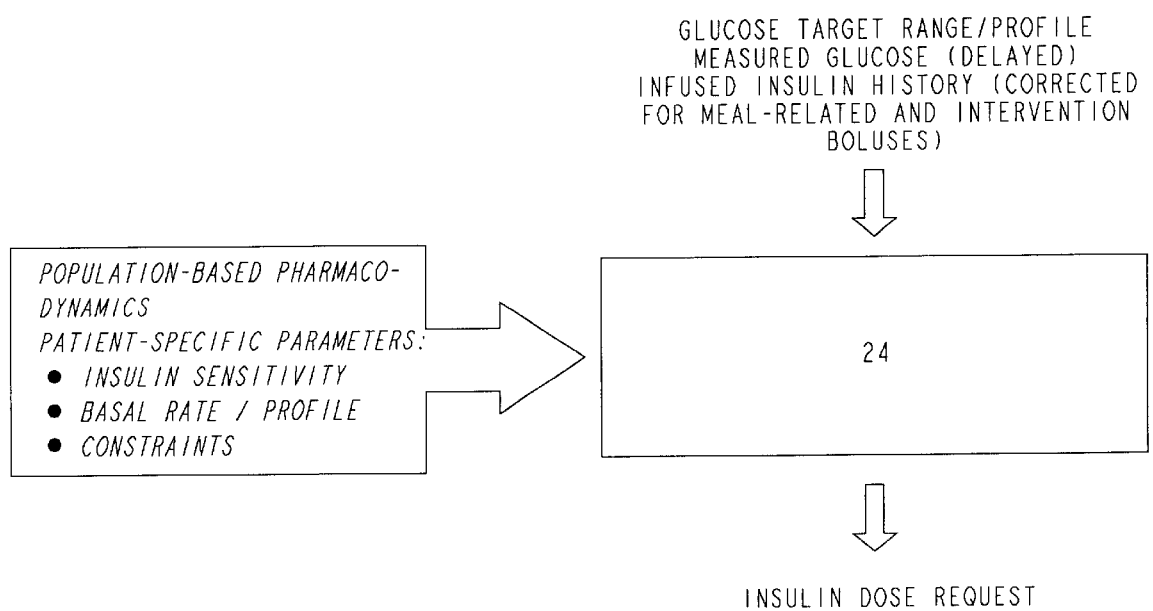
FIG. 8 is a schematic of a portion of the system of FIG. 5.

The memory unit can communicate with the processor and communication units through wired or wireless means (IR link or RF link). The processor unit of the control unit 14 predicts an expected drop in glucose over time after accounting for the time delay in the sensor using a feedback algorithm that is stored in the memory unit. Based upon that drop, the processor unit makes a recommendation for the administration of additional insulin to the subject to reach a pre-determined target glucose level at a pre-determined time in the future. In preferred embodiments, as will be discussed hereafter; the processor unit also uses a feedforward algorithm stored in the memory unit that allows adjustment due to variations in a subject's glucose-insulin dynamics as well as meal related information. See FIGS. 5, 7, and 8.

In at least one embodiment of the present invention, the control unit 14 operates using both levels of algorithms. The first level is a basal rate control or a feedback algorithm stored in the memory unit. The second level is a compensation control for meals and/or exercise or a feedforward algorithm that is also stored in the memory unit. See FIGS. 5, 7 and 8. It is appreciated that the feedback algorithm operates on the assumption that there exists an insulin basal rate for a subject that is required to maintain a steady-state glucose level at a specified therapy level. This pre-determined basal rate is used by the feedback algorithm in making its insulin dosage recommendations. The feedback algorithm excludes insulin equivalents for meals and exercise from the prediction of a future glucose value. Recommendations for doses of insulin to cover meals are made based upon the subject's experience (carbohydrate/insulin ratio or fixed dose) and lie outside of the feedback algorithms used by the control unit 14.

In the feedforward algorithm, the administered insulin dose is expected to ideally flatten or counteract the carbohydrates taken in the meal (or at least stay within a predetermined range of glucose values over a period of time). The feedforward algorithm reprocesses historical data of the subject to make a determination of an appropriate insulin dosage for categorized meals. Likewise, the insulin dose reduction due to exercise is based on historical data to determine the appropriate insulin dose reduction for categorized exercise. It is appreciated, that the feedback algorithm used by the processor unit of the control unit 14 does not see the effects of these feedforward meal-related insulin doses or exercise-related insulin reductions.

The control unit 14 uses the feedback algorithm in a predictive model to predict the future glucose level of a subject at a pre-determined time. The feedback algorithm is illustrated by equations (1–3). First, equation (1) is used to predict a current glucose value (for an expected delay in glucose measurement) as follows: (1)

$$G(i+1) = G(i) + \sum_{i=1}^{i-\frac{InsulinDuration}{\Delta T}} [(InsuTrace(i) * InsuGluDrop(i)) + BasalRequirement(i)] * Sensitivity$$

Wherein
 G (i)=glucose concentration i cycles in the past
 i=cycle
 InsuTrace (i)=series of pulses of insulin that were administered in the past (excluding meal-related insulin doses and exercise-related insulin reductions) normalized
 InsuGluDrop (i)=amount that the glucose is expected to drop on the next cycle due to insulin delivered at times in the past
 ΔT=time interval between cycles (in minutes)
 Basal Requirement (i)=amount of insulin required in the i'th cycle to maintain current glucose in the absence of disturbances
 Sensitivity=expected magnitude of glucose drop for 1U of insulin.

Next, control unit 14 predicts a future change in glucose level in accordance with equation (2):

(2) ΔG=—(TotalInsuRemain—BasalReq) * Sensitivity

Wherein
 ΔG=expected future change in glucose levels
 TotalInsuRemain=expected amount of insulin remaining in the subject's system (excluding meal-related doses and exercise dose reductions)
 BasalReq=how much insulin the subject is estimated to need Control unit 14 then makes a recommended insulin dose to reach the target range of glucose level in full time of the insulin action using equation (3):

(3) InsuRecommend=[G(0)+ΔG—Target]/Sensitivity+BasalNeedPerCycle

Wherein
 InsuRecommend=recommended insulin dosage
 G(0)=predicted current glucose level
 Target=glucose target level
 BasalNeedPerCycle=basal requirements of the subject during each cycle The recommended dosage is rounded to the nearest 0.05 U to 0.1 U resolution. It is appreciated that the recommended dosage need not be rounded or may be rounded to a different level of precision in accordance with the disclosure.

The recommendation of the control unit 14 resulting from the feedback algorithm is transmitted to the delivery unit 12. The transmission can take place over a fixed wire or preferably via telemetric connection (IR link or RF link). It is appreciated that the transmission can take place using any number of wired or wireless means in accordance with this disclosure. It is also possible that the subject may operate the delivery unit 12 themselves, such as an insulin pump outfitted with a transmission unit that transmits the administered insulin dose along with the time of administration to the control unit 14.

Figure 4:
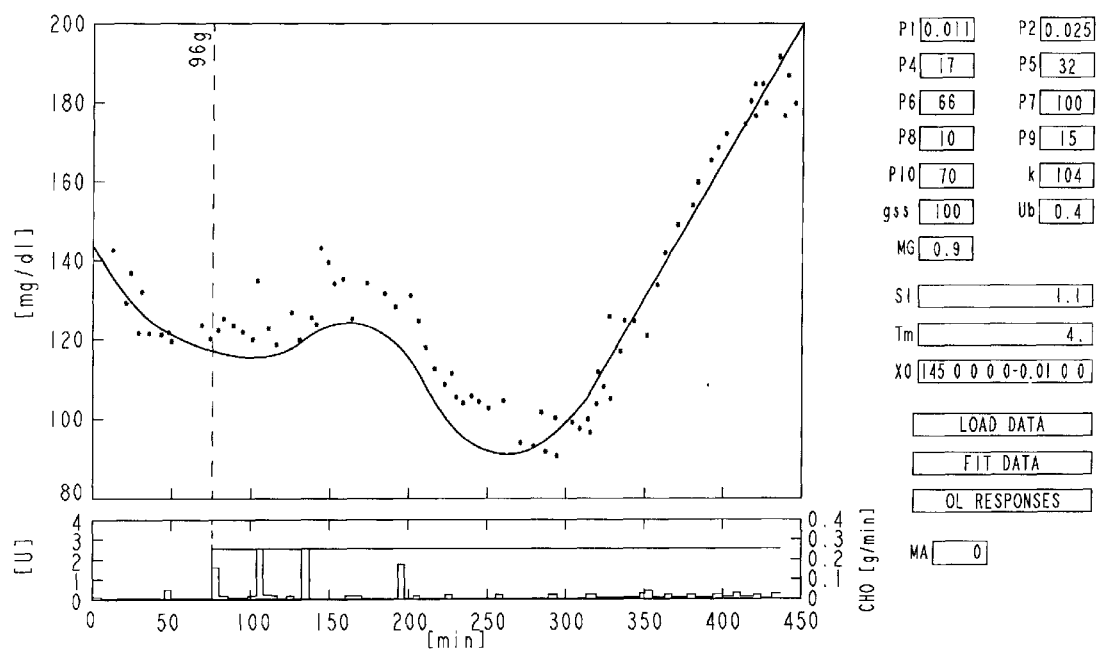
FIG. 4 is a schematic of the system utilizing the feedforward algorithm.

The feedforward algorithm is part of an insulin adaptation model used by unit 14 that allows the system to analyze past data and to make modifications to the existing therapy based upon that data. This adaptation model performs the function of an event handler 20, a meal compensator 22, a basal controller 24, and a dose nullifier 26. See FIG. 4. In practice, the adaptation model again assumes a basal insulin requirement and an insulin sensitivity, which is specific to the subject. It is appreciated that the subject initially inputs information on meals and exercise into control unit 14 based upon personal history. See FIG. 4, which is a schematic illustration of the feedforward algorithm of the adaptation model. The adaptation model uses this subject-provided data as well as the historical data gathered by the unit 14 to correct or refine the subject-provided data to make a recommended therapy as to the distribution and amount of insulin for meal related doses as well as exercise.

Thus, the adaptation model uses historical data for post processing to develop updated settings and functions for the particular subject. Specifically, the historical data is reprocessed by first mathematically removing all insulin from the dataset except for the particular subject's basal requirement of insulin. When the correct basal insulin rate(s) are applied, it is expected that the subject's glucose levels will remain nearly flat while fasting and for short pre-prandial periods. During meals, the glucose levels progressively increase with time and only during exercise is a decrease anticipated. Second, the distribution and amount of insulin doses are determined that provide a flat or sculpted daily glucose profile (target insulin delivery). Once the target insulin delivery is determined a meal-related insulin distribution profile is computed from an average response of reprocessed historical events for the particular subject.

The feedforward algorithm is used as part of an intensive insulin therapy/pump therapy and allows the control unit 14 to make adjustments due to variations in the subject's glucose-insulin dynamics as well as enables the control unit 14 to compensate for meals. This feedforward algorithm first makes an assumption that non-meal related insulin needs are covered by the basal rate. This basal rate has a fixed profile over the day. Disturbances due to meals are compensated for by insulin doses.

Therefore, in the cycle following the entry of meal information, the unit 14 will make an insulin dosage recommendation of the basal rate when the glucose values remain within a predefined post-prandial glucose range. Unit 14 in the upcoming cycles, will recommend that delivery unit 16 administer meal-related amounts of insulin based on the carbohydrate amount and speed entered by the subject into the unit 14. These meal-related insulin dose sizes are based on the unit's reprocessing of historical data of the subject. Specifically, the dose sizes are determined from the expected carbohydrate intake and the insulin-to-carbohydrate ratio. This intake may be constant or may be dependent based on the meal type or the time-of-day. Further assumptions include that insulin pharmacokinetics and pharmacodynamics are initially population based; the duration of the insulin effect is about 4 to about 6 hours; and there is an assumed shape of the insulin effect on the subject illustrated in FIG. 5. It is appreciated that these assumptions are merely guidelines and may vary in accordance with this disclosure. The various parameters are further illustrated in FIG. 7. The insulin effect curve is normalized to one. Further, the glucose lowering effect of a given insulin dose profile is calculated as the convolution of the insulin profile and the insulin effect curve, multiplied by the insulin sensitivity.

Unit 14 ignores the meal intake and any meal related insulin doses (except postprandial rise profile). Further, unit 14 reacts on the deviation of the predicted glucose concentration from the target range. Any insulin administered in excess of the basal need is expected to lower the glucose concentration and any insulin deficit is expected to raise the glucose concentration. Unit 14 estimates the expected drop / rise of glucose from the excess / deficit insulin, the normalized insulin effect, and the insulin sensitivity. The glucose target range can allow for a postprandial rise profile.

Figure 6:
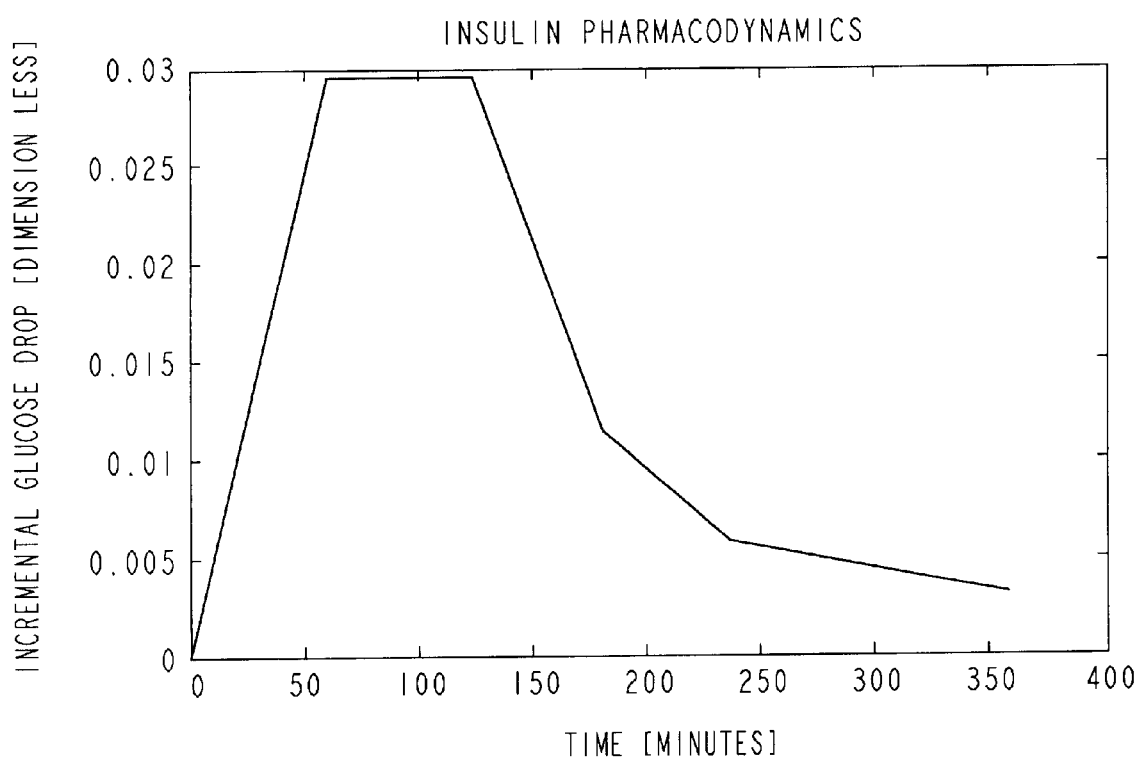
FIG. 6 is a schematic of a portion of the system of FIG. 4.

The feedforward algorithm of unit 14 is used to determine meal compensation/ dosing by equation (4):

(4) Dose=carbohydrates * insulin-to-carb-ratio * $\alpha_{meal\ type}$—intercept Wherein:
Dose=Total insulin dose
carbohydrates=grams of carbohydrates
insulin-to-carb-ratio=Insulin to Carbohydrate Ratio
$\alpha_{meal\ type}$=meal dependent scaling factor (meal compensator)
intercept=intercept to allow a linear fit for sizes of the meals The dose is distributed according to a predefined profile dependent on the user-input of carbohydrate amount and preferably the speed of the meal. The insulin distribution ranges from one to five doses depending on the meal size. It is appreciated, however, that the insulin distribution may vary to compensate for different meal speeds. Further, as shown in FIG. 6, the meal type is generally broken into meal type (breakfast, lunch, dinner, and snack), assuming that breakfast generally requires a relatively larger insulin dose than, for example, lunch, size (amount of carbohydrates), speed (glycemic index or composition: carbohydrates/ protein/fat) as well as the time of the meal. It is also appreciated that the intercept is often set close to zero. This intercept, however, is used as a way to initially under deliver insulin, or to set a threshold level of a meal to initiate the delivery of insulin to the subject.

There may also be constraints, which are defined by the equation (5): (5) infusion rate$\geq \beta$* basal rate. wherein $\beta$=a fraction that defines a minimum basal rate.

It is appreciated that $\beta$ ranges from about 0.25 to about 0.5. Preferably, p is 0.5. This constraint is generally used for overnight and is used to minimize excessive production of glucose from the liver. It is anticipated that the constraint can be violated if a large insulin dose has been administered recently, as well as when the subject is exercising. It is appreciated that this constraint is merely a guideline, and may vary in accordance with this disclosure.

In addition to sensor, delivery unit, and control unit, the system of the present invention may comprise additional components, which can be assembled in different ways. Non-limiting examples of additional components include: a feedback unit, a data processor unit, a communication unit, and a power source unit. These components can be assembled in one single device, or they can be discrete devices that communicate with each other through wired or wireless means (IR link or RF link). A suitable data processor unit may be, for example, a microprocessor, a portable laptop computer, or a mainframe computer. The communication unit or units can be of the type of a serial port, a RF port, an IR port, an ultrasound mode, or any number of commercially available communication units. The power source can be solar power, battery power (throw away or rechargeable), conventional AC power, or mechanical power in accordance with this disclosure.

EXAMPLE 1

Figure 2:
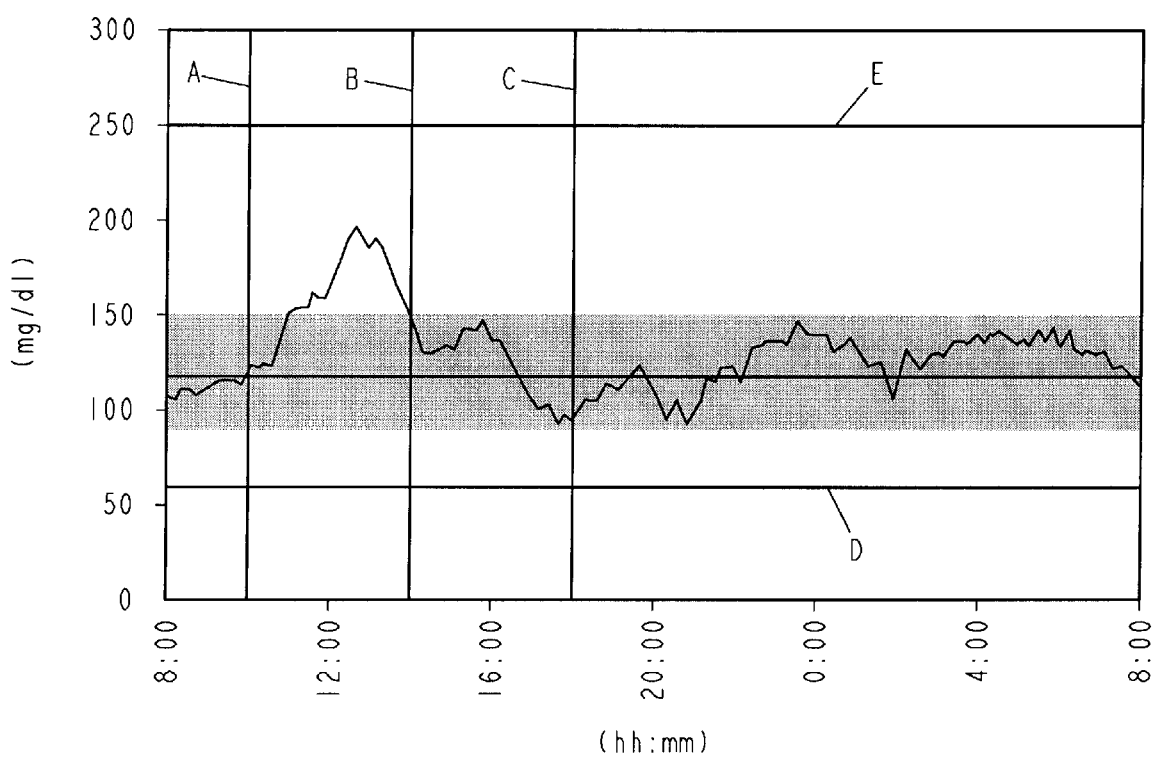
FIG. 2 is a graph showing an example of a glucose trace during a 24 hour control day with limited activity and three meals.

As shown in FIG. 2, glucose was traced for a subject during a 24 hour control day with limited activity and three meals. The first meal is shown by the vertical line A at 10:00, the second meal is shown by the vertical line B at 14:00 and the third meal is shown by the vertical line C at 18:00. The glucose value target range is shown by the vertical line D at 60mg/dL and line E at 250 mg/DL. The nominal target glucose value for the entire period was 120 mg/dL.

Figure 3:
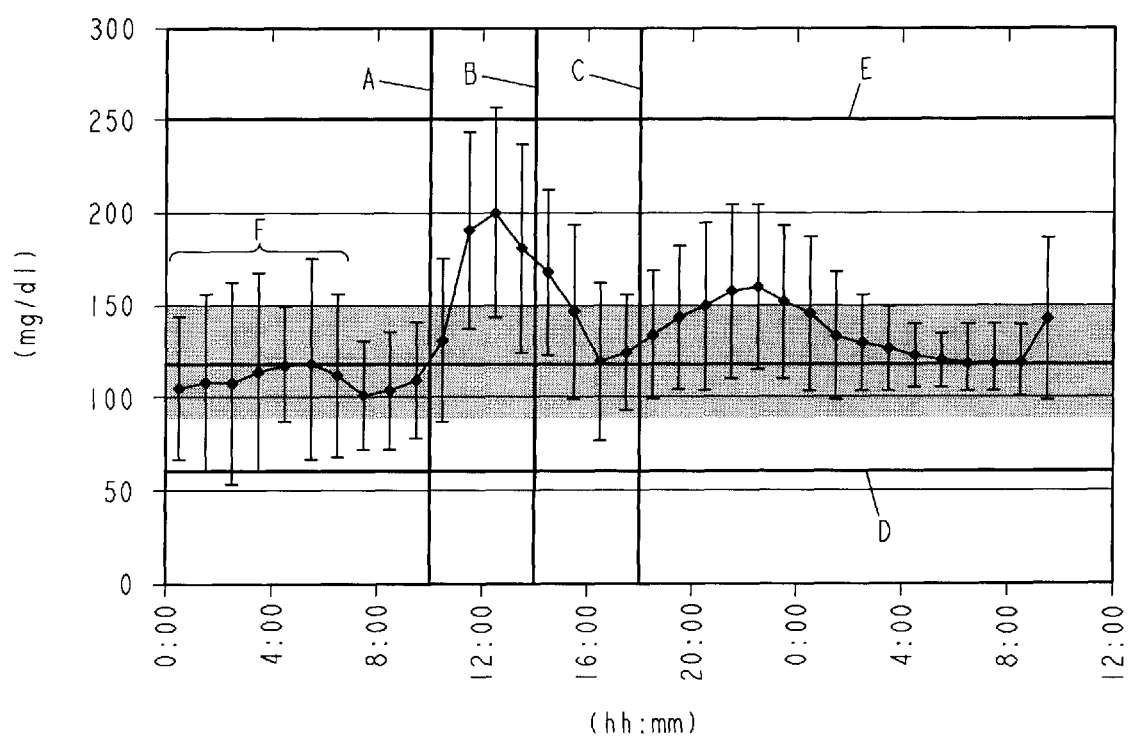
FIG. 3 is a graph showing the glucose concentration for 22 subjects over a single day where the amount of insulin dosed for each meal was computed from the subjects' insulin-to-carbohydrate ratio.

Referring now to FIG. 3, glucose concentration (average +/− one standard deviation) was plotted for 22 subjects, who were each controlled for one day. The meal dose was a single bolus at the time of the meal as shown by letters A,B,C, respectively and was based on the subject's insulin rules for the number of grams of carbohydrates in the meal. Lines D and E illustrate the glucose value target range. In addition, as shown in parenthesis F, the glucose concentration of the subjects was plotted from 0:00 to 8:00 before implementation of the system 10 in accordance with the present invention.

The parameters for the algorithm were composed of a set of population-based parameters and a set of individualized parameters based on the subjects' insulin therapy rules and logbook information. In this experiment, no adaptation to previous high-density glucose or insulin data was employed. Presumably better glycemic control could be achieved after adapting the insulin therapy based on the review of several days of algorithmic control.

The glucose concentration (average +/− one standard deviation) was plotted from a total of 30 experiments from 12 subjects, who were each controlled for at least one day. The meal doses were boluses beginning ten minutes before the time of the meal and were based on the computed insulin-to-carbohydrate ratios determined from the analysis of prior logbook data or control experiment data. The meals were of a fixed composition so that 60% of the calories in each meal came from carbohydrates.

Although the invention has been described in detail with reference to a preferred embodiment, variations and modifications exist within the scope and spirit of the invention as described and defined in the following claims.

What is claimed is:

1. A system for providing glycemic control to a subject, the system comprising:

an insulin delivery unit, a glucose sensor, and a control unit including a processor unit that receives glucose value readings from the glucose sensor, executes an algorithm that predicts a glucose value at a pre-determined time in the future, compares that predicted glucose value to a pre-determined glucose value range, and determines a corrective amount of insulin to be administered when the predictive glucose value lies outside of the pre-determined glucose value range and a communication unit that transmits the corrective amount to the delivery unit.

2. The system of claim 1 wherein the control unit is formed to accept data from the subject.

3. The system of claim 2 wherein the data includes information on size and type of a meal to be ingested and anticipated duration and intensity of exercise.

4. The system of claim 3 wherein the control unit includes a memory unit formed to store the data provided by the user.

5. The system of claim 4 wherein the memory unit also is formed to store an algorithm that utilizes the stored data and the processor unit is formed to execute the algorithm to determine the predictive glucose value.

6. The system of claim 1 wherein the sensor is a semi-continuous glucose-sensing unit.

7. The system of claim 1 wherein the algorithm includes the following equation:

$$\Delta G = -(\text{TotalInsuRemain} - \text{BasalReq}) * \text{Sensitivity}$$

wherein $\Delta G$=future change in glucose levels at a pre-determined time TotalInsuRemain=amount of insulin remaining in the subject's system at a current time, and BasalReq=how much insulin the subject is estimated to need to maintain the current glucose level, and Sensitivity=Insulin sensitivity.

8. The system of claim 7 further comprising a memory unit that is formed to store the algorithm and data, the data including glucose value readings from the glucose sensor, predicted glucose values, the pre-determined glucose value range, and corrective amounts of insulin.

9. The system of claim 8 wherein the memory unit is formed to store a feedforward algorithm that utilizes at least a portion of the data stored in the memory to compensate for meals.

10. The system of claim 9 wherein the feedforward algorithm includes the following equation:

$$\text{Dose} = \text{carbohydrates} * \text{insulin-to-carb-ratio} * \alpha_{meal\ type} - \text{intercept}$$

Wherein:

Dose=Total insulin dose carbohydrates=grams of carbohydrates insulin-to-carb-ratio=Insulin to Carbohydrate Ratio $\alpha_{meal\ type}$=meal dependent scaling factor intercept=intercept to allow a linear fit for sizes of the meals.

11. A system for providing glycemic control to a subject comprising:

a sensor formed to conduct a glucose measurement of a subject, a control unit including a processor unit that is formed to accept data from the subject on insulin sensitivity and basal rate, to execute an algorithm that generates a predictive value of the subject's glucose level at a predetermined time in the future based upon the glucose measurement from the sensor and the data, and to compute a corrective action when the predictive value lies outside of a predetermined target range, and an insulin delivery unit in communication with the control unit, the delivery unit being formed to administer automatically a dosage of insulin to the subject based upon the computed corrective action of the control unit.

12. The system of claim 11, wherein the control unit is formed to accept data from the subject regarding size and type of a meal to be ingested and anticipated duration and intensity of exercise.

13. The system of claim 11 wherein the algorithm includes the following equation:

$$\Delta G = -(\text{TotalInsuRemain} - \text{BasalReq}) * \text{Sensitivity}$$

wherein $\Delta G$=future change in glucose levels at a pre-determined time TotalInsuRemain=amount of insulin remaining in the subject's system at a current time, and BasalReq=how much insulin the subject is estimated to need at time, and Sensitivity=Insulin sensitivity.

14. The system of claim 11, wherein the control unit includes a memory that is formed to store data of the glucose concentrations as well as the time and amount of previously administered insulin.

15. The system of claim 14, wherein the memory is formed to store data regarding size and type of a meal to be ingested and anticipated duration and intensity of exercise of the subject.

16. A method for providing glycemic control to a subject, the method comprising the steps of:

determining the glucose value of a subject, inputting the glucose value into at least one processor, the at least one processor being formed to execute at least one algorithm formed to anticipate the future effects of insulin that has been previously delivered to the subject, to incorporate constraints on insulin delivery and glucose deviations, and to determine a corrective amount of insulin to be administered when the predictive glucose value lies outside of the pre-determined glucose value range, automatically delivering the corrective amount of insulin to the subject, and repeating the determining and inputting steps.

17. The method of claim 16 wherein the inputting step includes providing data on size and type of a meal to be ingested t.

18. The method of claim 17 wherein the inputting step includes providing data on anticipated duration and intensity of exercise.

19. A system for providing glycemic control to a subject, the system comprising:

means for delivering insulin to a subject, means for determining a glucose value from the subject, and a control unit including a processor unit that is formed to compare the glucose value to a pre-determined glucose value range, to determine a corrective amount of insulin to be administered when the predictive glucose value lies outside of the pre-determined glucose value range, and to transmit the corrective amount to the delivering means.

20. A system for predicting a future glucose value of a subject at a predetermined time, the system comprising a control unit that comprises:

a processor unit formed to predict the future glucose value with an algorithm

ΔG=—(TotalInsuRemain—BasalReq) * Sensitivity wherein ΔG=future change in glucose levels at a predetermined time, TotalInsuRemain=amount of insulin remaining in the subject's system at a current time, and BasalReq=how much insulin the subject is estimated to need to maintain the current glucose level, and Sensitivity=Insulin sensitivity, and wherein the processor makes a recommended insulin dose to reach a target range in full time of the insulin action according to the following equation:

InsuRecommend=[G(0)+ΔG–Target]/Sensitivity+BasalNeed PerCycle wherein InsuRecommend=recommended insulin dosage, G (0)=predicted current glucose level, Target=glucose target level, and BasalNeed PerCycle=basal requirements of the subject during each cycle.

21. The system of claim 20 wherein the processor is further formed to compensate for meals and exercise with a feedforward algorithm Dose=carbohydrates * insulin-to-carb-ratio * $\alpha_{meal\ type}$—intercept wherein Dose=Total insulin dose, carbohydrates=grams of carbohydrates, insulin-to-carb-ratio=Insulin to Carbohydrate Ratio, $\alpha_{meal\ type}$=meal dependent scaling factor, and intercept to allow a linear fit for sizes of the meals.

22. The system of claim 21 wherein the processor is further formed to provide a constraint to the feedforward algorithm, wherein the constraint is defined by the following equation: infusion rate $\geq \beta$* basal rate, wherein $\beta$=a fraction that defines a minimum basal rate.

23. The system of claim 20 wherein the processor predicts a current glucose value using the following equation:

$$G(i+1) = G(i) + \sum_{i=1}^{i=\frac{InsulinDuration}{\Delta T}} [(InsuTrace(i) * InsuGluDrop(i)) + BasalRequirement(i)] * Sensitivity$$

wherein G (i)=glucose concentration i cycles in the past, i=cycle, InsuTrace(i)=series of pulses of insulin that were administered in the past (excluding meal-related insulin doses and exercise-related insulin reductions) normalized, InsulinDuration=total time action of insulin, InsuGluDrop (i)=amount that the glucose is expected to drop on the next cycle due to insulin delivered at times in the past, ΔT=time interval between cycles (in minutes), Basal Requirement (i)=amount of insulin required in the i'th cycle to maintain current glucose in the absence of disturbances, and Sensitivity=expected magnitude of glucose drop for IU of insulin.

24. A system for recommending an insulin dose to compensate for meals of a subject, the system comprising a control unit that comprises:

a processor formed to compensate for meals with a feedforward algorithm

Dose=carbohydrates * insulin-to-carb-ratio * $\alpha_{meal\ type}$—intercept wherein Dose=Total insulin dose, carbohydrates=grams of carbohydrates, insulin-to-carb-ratio=Insulin to Carbohydrate Ratio, $\alpha_{meal\ type}$=meal dependent scaling factor, and intercept to allow a linear fit for sizes of the meals.

25. The system of claim 25 wherein the processor is further formed to provide a constraint to the feedforward algorithm, wherein the constraint is defined by the following equation: infusion rate $\geq \beta$* basal rate, wherein $\beta$=a fraction that defines a minimum basal rate.

* * * * *